US010529212B2

(12) United States Patent
Ribble et al.

(10) Patent No.: US 10,529,212 B2
(45) Date of Patent: Jan. 7, 2020

(54) SYSTEM FOR PREDICTING DEPARTURE FROM AN ORIGIN BASED ON EXTERNAL FACTORS

(71) Applicant: Hill-Rom Services, Inc., Batesville, IN (US)

(72) Inventors: David L. Ribble, Indianapolis, IN (US); Kirsten M. Emmons, Batesville, IN (US); Yongji Fu, Harrison, OH (US)

(73) Assignee: HIll-Rom Services, Inc., Batesville, IN (US)

( * ) Notice: Subject to any disclaimer, the term of this patent is extended or adjusted under 35 U.S.C. 154(b) by 147 days.

(21) Appl. No.: 15/388,535

(22) Filed: Dec. 22, 2016

(65) Prior Publication Data

US 2017/0358193 A1    Dec. 14, 2017

Related U.S. Application Data

(60) Provisional application No. 62/347,324, filed on Jun. 8, 2016.

(51) Int. Cl.
*G08B 21/04* (2006.01)
*A61G 7/05* (2006.01)
*A61G 12/00* (2006.01)

(52) U.S. Cl.
CPC ....... *G08B 21/0461* (2013.01); *A61G 7/0507* (2013.01); *A61G 12/00* (2013.01); *A61G 2203/10* (2013.01); *A61G 2205/60* (2013.01)

(58) Field of Classification Search
CPC ... G08B 21/0461; A61G 7/0507; A61G 12/00
See application file for complete search history.

(56) References Cited

U.S. PATENT DOCUMENTS

| 9,041,810 B2 | 5/2015 | Ecker et al. |
| 2005/0182305 A1 | 8/2005 | Hendrich |
| 2007/0132597 A1 | 6/2007 | Nydegger et al. |

(Continued)

FOREIGN PATENT DOCUMENTS

| EP | 2508128 A1 | 10/2012 |
| JP | 2009268790 A | 11/2012 |

(Continued)

OTHER PUBLICATIONS

European Search report reference P/76464.EP01 Application No./Patent No. 17152025.7-1657; dated Jul. 17, 2014.

(Continued)

*Primary Examiner* — Curtis B Odom
(74) *Attorney, Agent, or Firm* — Kenneth C. Baran

(57) ABSTRACT

One embodiment of a monitoring system includes a sensing subsystem adapted to sense an external parameter within a region of interest relative to an occupant support or an occupant of the occupant support. The monitoring system also includes a processor. The processor is adapted to receive data representing the sensed external parameter and to execute machine readable instructions thereby causing the monitoring system to evaluate, based on the received data, a likelihood that the occupant will attempt an egress from the occupant support. The processor is also adapted to generate a notification of the likelihood of attempted egress.

19 Claims, 11 Drawing Sheets

(56) References Cited

U.S. PATENT DOCUMENTS

| | | | |
|---|---|---|---|
| 2009/0119843 A1* | 5/2009 | Rodgers | A61B 5/1115 5/611 |
| 2009/0268790 A1 | 10/2009 | Josiam et al. | |
| 2013/0246088 A1 | 9/2013 | Huster et al. | |
| 2015/0109442 A1 | 4/2015 | Derenne et al. | |

FOREIGN PATENT DOCUMENTS

| | | |
|---|---|---|
| WO | 2012040554 A2 | 3/2012 |
| WO | 2013052123 A1 | 4/2013 |

OTHER PUBLICATIONS

Social-aware and context-aware multi-sensor fall detection platform; Femke De Backere, Femke Ongenae, Floris Van den Ageele, Jeroen Hoebeke, Stijn Verstichel, Ann Ackaert, and Filip De Turck; Department of Information Technology (INTEC). Ghent University=iMinds, Gaston Crommelaan 8 bus 201, B-9050 Ghent, Belgium; 4-pages.

ResearchGate; Risk factors in falls among the older according to extrinsic and intrinsic precipitating causes; Article in European Journal of Epidemiology—Feb. 2000; Impact Factor:5.34—DOI: 10.1023/A:/1007636531965—Source: PubMed; Available from: J.J Jimenez-Moleon Retrieved on: May 8, 2016; 12-pages.

Response dated Jun. 13, 2018; European Patent application No. 17152025.7; System for Predicting Departure from an Origin Based on External Factors; Ref: P/76464.EP01/AF/gh; 2-pages.

Claims track changes; Jun. 13, 2018; 4-pages.

Claims final; Jun. 3, 2018; 4-pages.

Amended pages track changes; Monitoring System and Method; Jun. 13, 2018; 3-pages.

Amended pages final; Monitoring System and Method; Jun. 13, 2018; 2-pages.

* cited by examiner

US 10,529,212 B2

SYSTEM FOR PREDICTING DEPARTURE FROM AN ORIGIN BASED ON EXTERNAL FACTORS

TECHNICAL FIELD

The subject matter described herein relates to a system for predicting departure of a person from a place of origin based on factors external to the place of origin. In one example application the place of origin is an occupant support such as a hospital bed, a stretcher, a procedural chair and a patient chair, to name just a few examples, and the person is the patient or occupant of the bed.

BACKGROUND

Hospital patients are not always authorized to exit their beds without assistance. It is therefore desirable to predict the likelihood that a given patient will exit her bed when not permitted to do so. It is also desirable to issue a notification so that a caregiver can intervene to prevent an unauthorized exit (also referred to as an unauthorized egress).

Some systems described in the literature predict egress by monitoring the position of the patient on the bed. One example of such a system is described in U.S. Pat. No. 6,208,250. Other systems predict egress as a function of the state of the bed itself, for example whether the bed is adjusted to a low elevation or a high elevation and/or whether or not siderails are deployed or stowed. Examples of such systems are described in U.S. patent application Ser. No. 15/000,258 entitled "Method of Predicting Occupant Egress from an Occupant Support Based on Perimeter Panel Status and Occupant Location, and a Related Apparatus" filed on Jan. 19, 2016 and U.S. Provisional Patent Application 62/289,638 entitled "Apparatus and Method of Assessing the Status of an Occupant of an Occupant Support Based on Forces Exerted on a Perimeter Panel of the Occupant" filed on Feb. 1, 2016. Despite the merits of these systems, they do not consider the effect of factors external to the bed. These external factors may be instrumental in motivating or inspiring a patient to exit the bed, even if she is not authorized to do so without assistance. Therefore consideration of these factors may improve the accuracy and timeliness of egress predictions.

SUMMARY

The present invention may comprise one or more of the features recited in the appended claims and/or one or more of the following features or combinations thereof.

A monitoring system includes a sensing subsystem adapted to sense an external parameter within a region of interest relative to an occupant support or an occupant of the occupant support. The monitoring system also includes a processor. The processor is adapted to receive data representing the sensed external parameter and to execute machine readable instructions thereby causing the monitoring system to evaluate, based on the received data, a likelihood that the occupant will attempt an egress from the occupant support. The processor is also adapted to generate a notification of the likelihood of attempted egress.

A second embodiment of a monitoring system includes a memory containing information about a region of interest relative to an occupant support. The second embodiment also includes a processor. The processor is adapted to accept the information about the region of interest of the occupant support from the memory and to receive data representing at least one external parameter which is not included in the information about the region of interest stored in the memory. The process is also adapted to execute machine readable instructions thereby causing the monitoring system to evaluate, based on the accepted information and received data, a likelihood that an occupant of the occupant support will attempt egress from the occupant support. The processor is also adapted to generate a notification of the likelihood.

BRIEF DESCRIPTION OF THE DRAWINGS

The foregoing and other features of the various embodiments of the system for predicting patient described herein will become more apparent from the following detailed description and the accompanying drawings in which.

DETAILED DESCRIPTION

Figure 1:
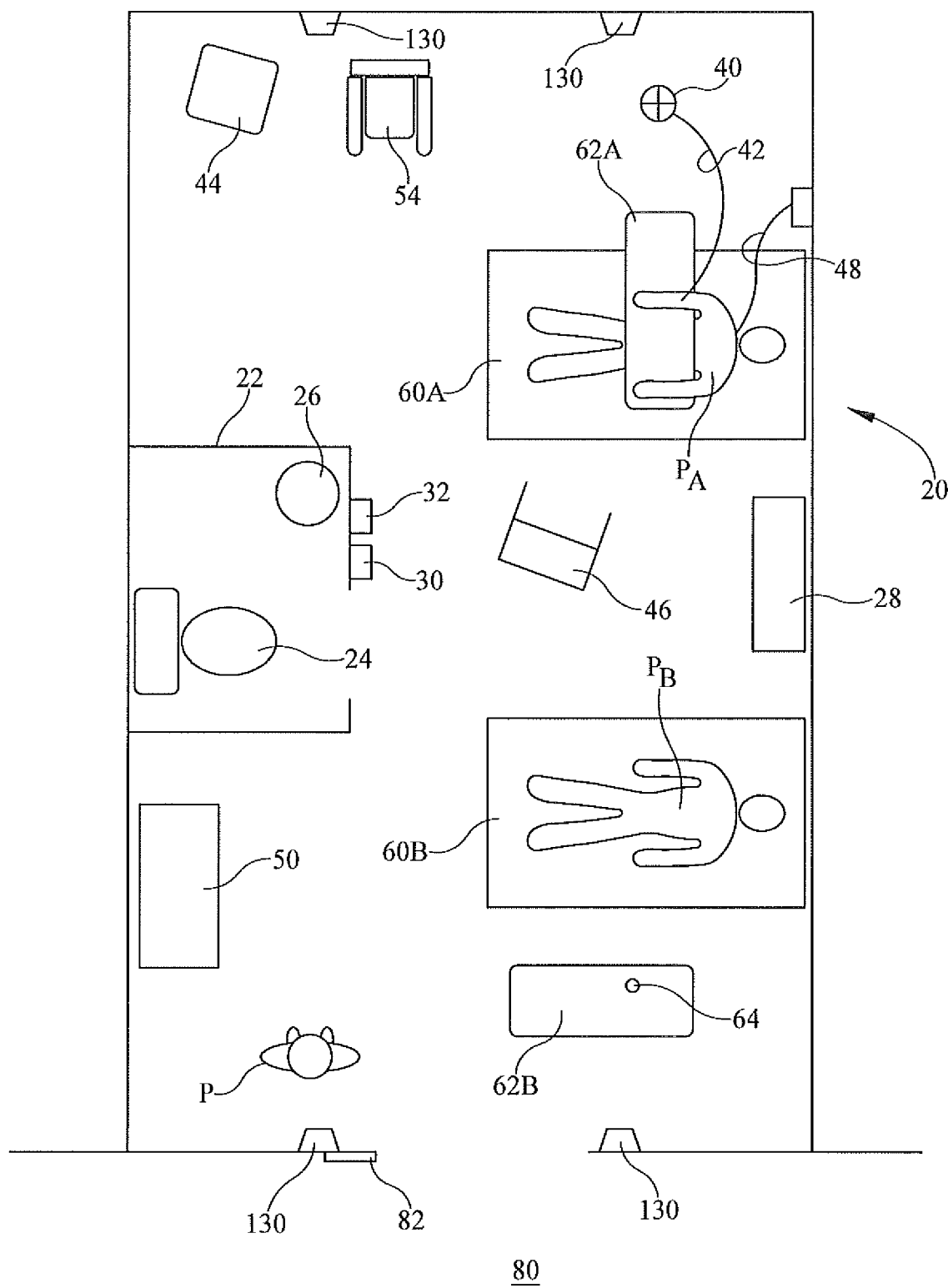
FIG. 1 is a plan view of a hospital room showing a variety of objects typically found in a hospital room.

FIG. 1 is a schematic plan view of a hospital room and a sampling of items or objects which may be present in the room. These include inanimate objects which are spatially fixed such as a lavatory 22 with a toilet 24 and sink 26, a built-in storage cabinet 28, a wall mounted thermostat 30 and a wall mounted light switch 32. The sampling of objects also includes inanimate movable objects such as an IV pole 40, IV line 42, equipment cart 44, walker 46, free standing storage cabinet 50, portable chair 54, beds 60A, 60B, over-bed tables 62A, 62B, and a glass of water 64. The IV pole, equipment cart, and over-bed tables are designed to be easily moved and include wheels or casters, not visible, to facilitate ease of movement. Whether or not these objects are present in the room, and their location if they are present, is therefore not highly predictable. The IV line 42, walker 46, oxygen line 48 portable chair 54, and glass 64 are light weight and intended to be moved and therefore their presence, and their location if they are present, is also not highly predictable. The free standing cabinet can be moved, but is not designed or intended to be easily and routinely movable. Therefore its location in the room, assuming it is present, is more predictable. The beds may be movable, however their location in a hospital room is usually predictable with a high degree of confidence due to the layout of the room and the location of utilities such as electrical outlets and outlets for medical gases.

The illustration also shows animate objects including patient $P_A$ sitting up in bed 60A and patient $P_B$ lying in bed 60B. Each patient is also referred to herein as an occupant of her assigned bed (bed 60A for patient $P_A$ and bed 60B for patient $P_B$). Another animate object in the room is person P who is a non-patient. Examples of non-patients include hospital staff members such as nurses, doctors, orderlies, meal service staff, housekeepers, maintenance personnel, clergy, law enforcement officers, and patients' friends, acquaintances and family members to name just a few.

The room defines a region of interest with respect to each patient or with respect to her bed. In the context of predicting egress based on external parameters as described herein, no distinction is made between the occupant and the occupant support. This is because the occupant is assigned to the bed and is presumed to be occupying it. Therefore the relationship between an external parameter and the bed (e.g. proximity of a lavatory or the presence and source of an annoying noise) does not differ in any meaningful way from the relationship between the external parameter and the occupant.

Except for patient $P_A$ and bed 60A the objects in the room, i.e. in the region of interest, are considered to be external to bed 60A. Likewise, except for patient $P_B$ and bed 60B the objects in the room are considered to be external objects with respect to bed 60B. In other words all the objects in the room are external to both of the beds except that neither bed is considered to be external to itself and neither patient is considered to be external to her bed. A property of an external object which is relevant to predicting patient egress from a bed as disclosed herein is referred to as an external parameter. Object related external parameters include knowledge of the presence or absence of an object, its identity (e.g. chair, person, glass), its location and its state of motion.

Objects which are inherent, commonplace components of hospital beds are not considered to be external objects. Examples of such components include the bed frame, mattress, headboard, footboard, siderails, and the various mechanical and electrical components provided to adjust the elevation, inclination and profile of the bed. Some of these components might be designed to be easily removable. For example the footboards of some beds are readily removable in order to facilitate authorized occupant egress from the foot end of the bed when the bed is adjusted to a chair-like profile. The removable nature of such components does not cause them to be external objects. This is because they are commonplace features of most beds, are in place on the bed most of the time, and are removed only temporarily and for a definite purpose, such as removing the footboard to facilitate egress as in the foregoing example.

Other objects may not be inherent, commonplace components of hospital beds, but nevertheless are excluded from the class of external objects. Examples include oxygen tanks which may be placed in a recess on the bed frame similar to an automotive cup holder. Although the oxygen tank is not an inherent, commonplace component of most hospital beds, it is supported on the bed and is provided on an as-needed basis to serve the needs of selected patients rather than the needs of a broad spectrum of patients. Other examples of objects which are not considered to be external objects are a climate management topper temporarily placed on the mattress to meet the needs of a patient at high risk of developing pressure ulcers and its power pack unit, which may be temporarily attached to the footboard.

Some of the external objects in the region of interest may influence the likelihood that an occupant will attempt to make an unauthorized exit from her bed. Ambient conditions in the room or other region of interest may also affect the likelihood of an unauthorized exit. Ambient parameters include air temperature, humidity, artificial and natural light, sound, and air currents (drafts) perceivable by patient $P_A$ or $P_B$. The ambient parameters, like the object related parameters described above, are considered to be external parameters.

Figure 2:
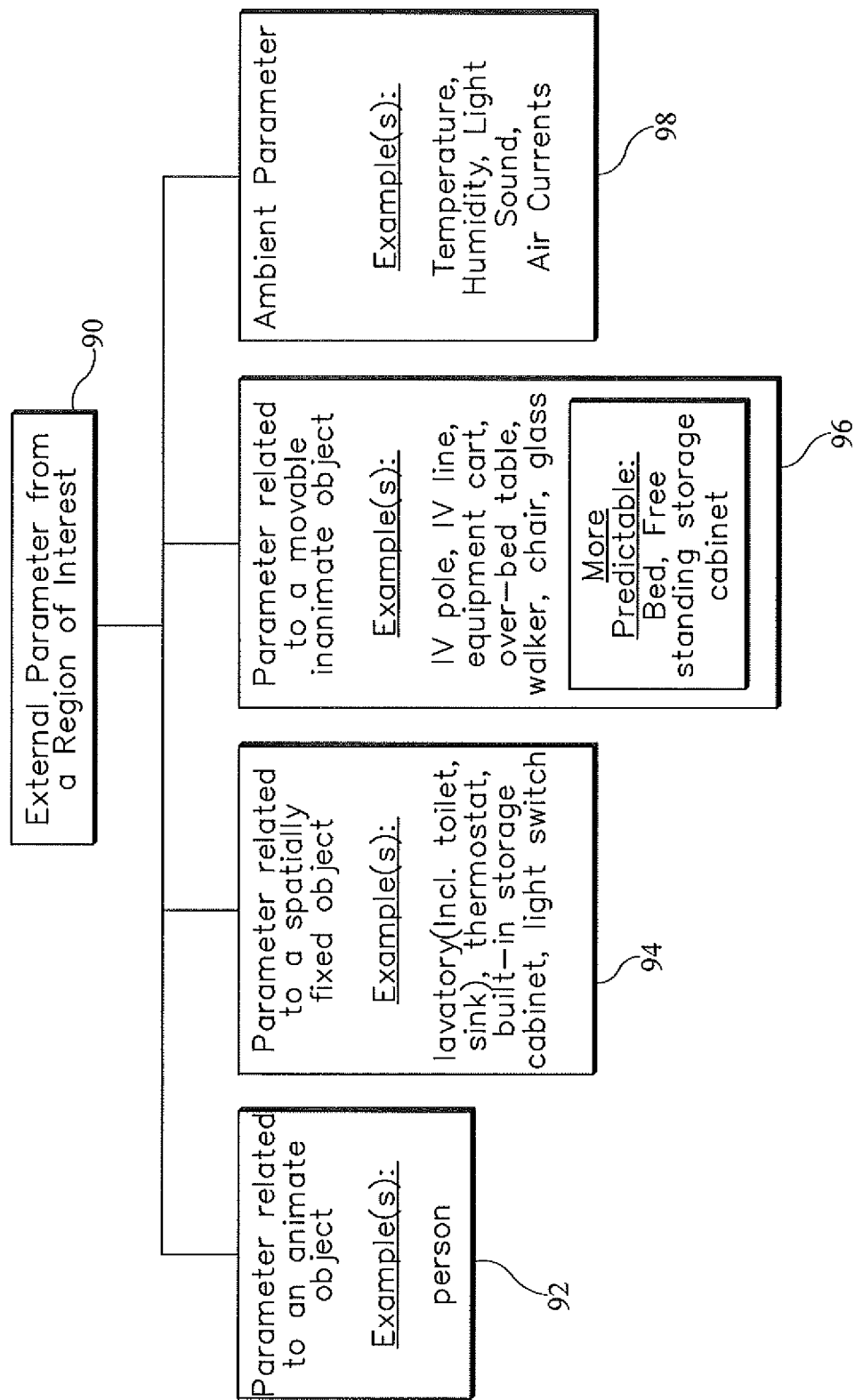
FIG. 2 is a taxonomical chart showing four classes of external parameters and at least one example parameter in each class.

FIG. 2 is a hierarchy or taxonomical chart showing that the external parameters (box 90) include parameters related to animate objects in the region of interest (box 92), parameters related to spatially fixed, inanimate objects in the region of interest (box 94), parameters related to movable inanimate objects in the region of interest (box 96) and ambient parameters (box 98). The chart also shows a non-exhaustive list of examples in each of the four classes of parameters.

The following examples illustrate how some of the above identified external parameters can influence the likelihood of unauthorized egress from the bed.

Consider first the inanimate, spatially fixed objects. The presence of lavatory 22 may encourage the patient to exit the bed, especially if the distance between the bed and the lavatory is short enough that the patient feels she is capable of reaching the lavatory without assistance. The built in storage cabinet 28 may also serve as an inducement to exit the bed if it contains items the patient wishes to access, or if the patient believes it contains such items. The presence of the light switch 32 and thermostat 30 may also encourage an unauthorized exit if the patient is bothered by light or temperature.

Next consider the inanimate movable items. Chair 34 may encourage patient $P_A$ to exit her bed in order to experience a change of surroundings or to be more comfortable. Walker 46 is an obvious motivation for the patient to exit the bed. The glass of water 64 may encourage patient $P_B$ to exit bed 60B if she is thirsty and the glass is out of reach from her position on the bed. Over-bed table 60B may also encourage egress if the patient perceives it to be a means of support. Conversely, table 60A, positioned as it is over patient $P_A$, may dissuade egress. Whether or not an inanimate movable object deters or invites egress may also depend on the location of the object relative to the occupant support or relative to the occupant herself while occupying the occupant support. For example walker 46 and chair 54 may be more likely to encourage the egress of patient $P_A$ if they are nearby patient $P_A$ as shown and less likely to encourage the egress of patient $P_A$ if they are remote from patient $P_A$, for example near doorway 70. Oxygen line 48 may be a deterrent to egress if it causes the patient to feel tethered to the facility wall.

Next consider the animate external objects, e.g. person P and patient $P_B$ from the viewpoint of patient $P_A$, or person P and patient $P_A$ from the viewpoint of patient $P_B$. If person P is identifiable by the patient as a member of the hospital staff, or as a person acting on behalf of the hospital's management, the patient may view person P as an authority figure, and therefore be dissuaded from exiting the bed. There may be a gradation of perceived authoritativeness. For example a person P identifiable as a nurse or doctor may be perceived by the patient as more authoritative than, say, a person P identifiable as an orderly. An orderly may be perceived as more authoritative than a member of the meal service staff, housekeeping staff or maintenance staff. The greater the perceived authority of person P, the lower the likelihood that the patient will attempt an unauthorized egress while that person is present. If the person P is not perceived as acting on behalf of hospital management, the patient may be either more or less inclined to exit the bed than would be the case if the person P were perceived as acting on behalf of hospital management. For example if the person is a friend the patient may be comforted by the friend's presence, and therefore may be deterred from attempting an unauthorized egress. On the other hand the patient may perceive the friend as unaware of the directive to not exit the bed without the assistance of a professional caregiver or as lacking authority to enforce the directive. The patient may therefore be more inclined to exit the bed.

When the likelihood of occupant egress depends on a person P, it may also depend on that person's state of motion. For example if a caregiver is present in the room, his presence is a strong deterrant to the patient attempting an unauthorized egress. If the patient loses sight of the caregiver, but hears the caregiver's footsteps moving away from the room, the patient may conclude that the caregiver will not be present again anytime in the near future, and therefore may be more likely to attempt an unauthorized egress. Conversely if the patient hears approaching footsteps and believes those footsteps signal the impending arrival of a caregiver, the patient may be less inclined to attempt egress. In this case the region of interest extends beyond the room itself to include that portion of the adjoining corridor 80 within range of microphone 82 which is mounted on the wall just outside the room.

The ambient parameters may also influence the likelihood of egress. If the ambient parameters are such that the patient is uncomfortable (too hot or cold, disturbed by humidity, light, noise, or a draft) the patient may be motivated to exit the bed in order to adjust the thermostat, turn a light off or close a drape, remedy a noise, or deal with the draft, thus increasing the likelihood of unauthorized egress. This may be particularly true if the means to remedy the discomfort is readily apparent, such as the presence of a thermostat, light switch or drape. Conversely, if the patient is not uncomfortable as a result of external ambient parameters, she may be considered to be less likely to exit the bed on the basis of ambient factors.

Figure 3:
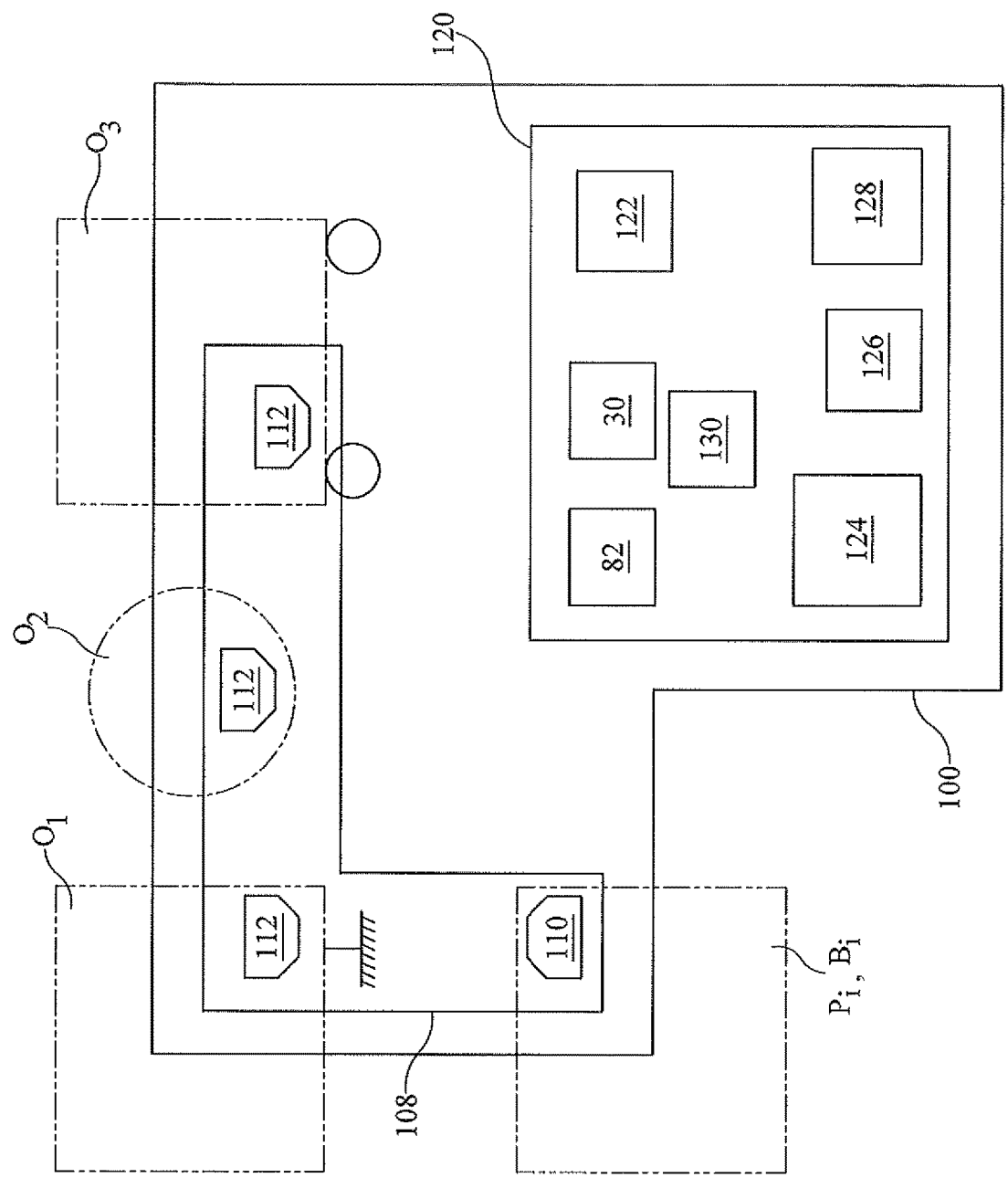
FIG. 3 is a schematic showing an example of a sensing subsystem adapted to sense an external parameter within a region of interest relative to an occupant support or relative to an occupant of the occupant support.

Referring additionally to FIG. 3, a monitoring system includes a sensing subsystem 100 adapted to sense an external parameter within a region of interest relative to an occupant support or relative to an occupant of the occupant support. (As noted above, in the context of predicting egress based on external parameters as described herein, no meaningful distinction is made between the occupant and the occupant support.)

In one embodiment sensing subsystem 100 comprises a suite 108 of RFID components such as RFID readers and tags. In FIG. 3 the suite of RFID components includes an RFID reader or interrogator 110 associated with the bed or the occupant of the bed and whose physical location corresponds closely to that of the bed or occupant. For example the RFID reader may be secured to the bed or may be a component of a wristband worn by the occupant for the duration of her stay in the hospital. In FIG. 3 the bed or patient is indicated by generic identifiers $B_i$ and $P_i$ and is illustrated with a dash-dot line to emphasize that the bed and patient are not part of the sensing subsystem. The sensing subsystem also includes an RFID tag or transponder 112 associated with an external object of interest and whose location closely corresponds to the external object of interest. In FIG. 3 the external objects of interest are designated by $O_1$ (representing a spatially fixed inanimate object), $O_2$ (representing an animate object) and $O_3$ (representing a movable inanimate object) and are illustrated with a dash-dot line to emphasize that the external objects are not part of the sensing subsystem. In the interest of economy and convenience of expression the RFID reader(s) and tag(s) may be described hereinafter as "attached" to the bed, patient or external object rather than being described as "whose location closely corresponds to . . . ". Thus, an RFID reader pinned to a patient's pajamas is considered to be attached to the patient even though it is not literally attached to the patient. Likewise an RFID tag incorporated into a nurse's identification badge (which badge is presumed to be clipped to the nurse's uniform while he is on duty) is considered to be attached to the nurse.

In operation the RFID reader 110 and tag 112 cooperate to reveal the presence (or absence) of the external object. The tag may be coded with information that reveals not only the presence of the object, but also its identity, e.g. to distinguish among a person, a water glass, a walker, and so forth. The tag may also be coded with information revealing an attribute of the object. For example if the object is a member of the hospital staff, the tag may indicate the staff member's role (e.g. doctor, nurse, orderly, nurses' aide, housekeeper, maintenance person). In the foregoing example the object is a person, the object's identity is that of a staff member, and the attribute is the staff member's role. Knowledge of the staff member's role allows the system to distinguish between individuals who a typical patient would view as an authority figure and individuals who a typical patient would view as a non-authority figure. As already noted a sharp distinction between authority figures and non-authority figures need not be drawn. Instead, the authoritativeness of a person could be graduated based on his or her role. In another example if the object is a visitor rather than a staff member, an RFID tag on the visitor's visitor badge might be coded to reveal that fact and possibly to assign an authority score or an authority status (authoritative or nonauthoritative) to that person. Although the foregoing examples are examples of attributes associated with a person, attributes of inanimate objects can be coded on RFID tags attached to those inanimate objects.

Another example of a movable inanimate object to which an RFID tag can be mounted is an intermittent pneumatic compression (IPC) sleeve. IPC's are sleeves that fit around a limb, such as a patient's calf. The sleeve is connected by a tube to an air source which periodically pressurizes and depressurizes the sleeve thereby periodically squeezing the patient's limb. The intermittent squeezing can help prevent the formation of blood clots. The presence of the tube connecting the sleeve to the air source may cause the patient to feel tethered to the bed and therefore may discourage egress.

Another example of a movable inanimate object to which an RFID tag can be mounted is fall risk stockings. Fall risk stockings are stockings which attract attention, for example by being of a bright color (e.g. bright red). If a patient who is at high risk of falling exits the bed, the bright color attracts the attention of hospital staff members who immediately recognize that the patient should not be out of bed without being accompanied. A patient wearing such stockings, and knowing that her unauthorized egress will attract attention, may be discouraged from exiting the bed.

The illustrated sensing subsystem also includes sensors to sense ambient parameters within the region of interest. These include microphone 82, a temperature sensor (which may or may not be the same as thermostat 30), a humidity sensor 122, a light sensor 124, a sound sensor 126, a sensor 128 to sense air currents (e.g. by sensing air speed and direction) in order to monitor for drafts, and depth sensors 130 to establish distances between objects.

Figure 4:
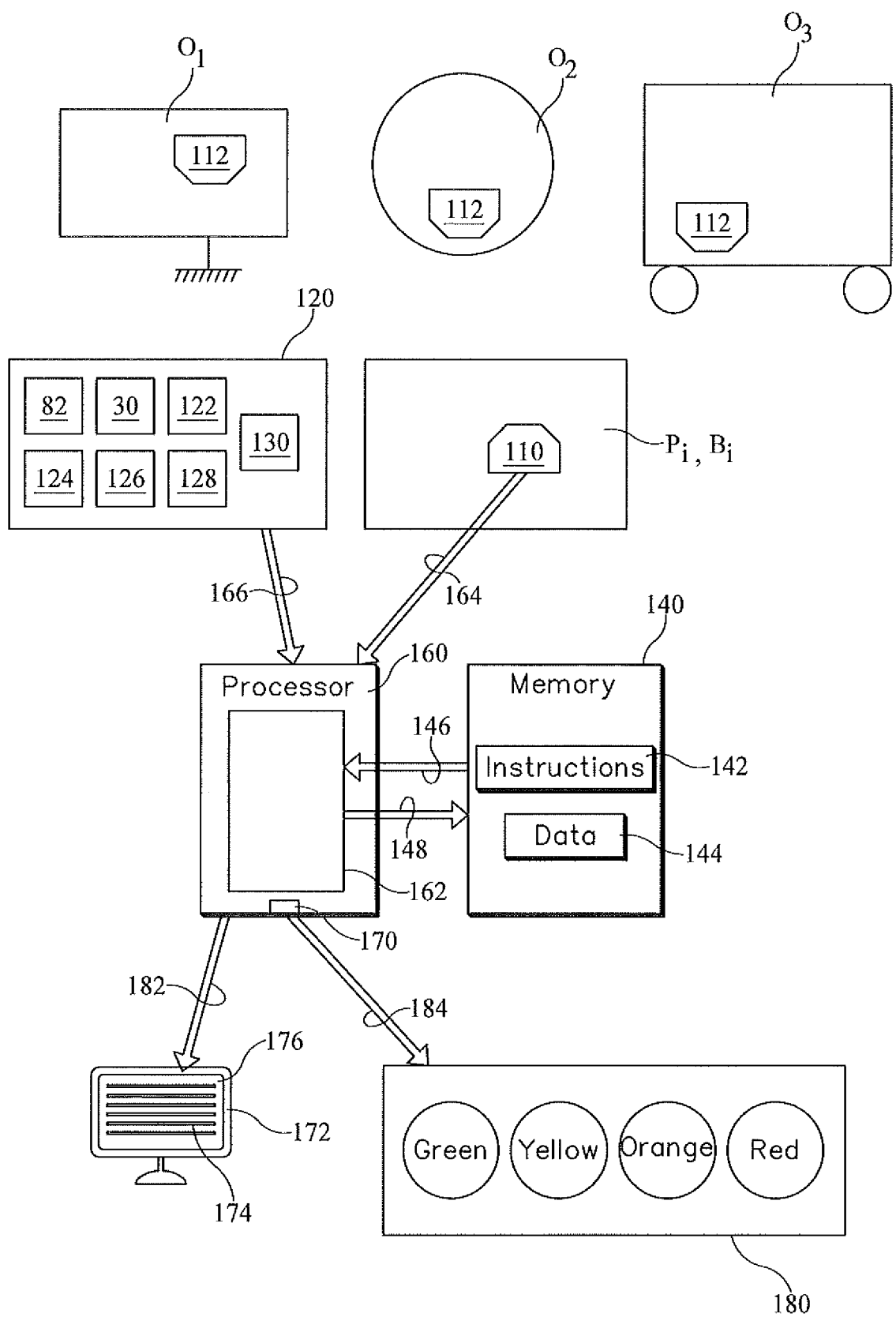
FIG. 4 is a schematic of a monitoring system for predicting patient egress from a hospital bed and which incorporates the sensing subsystem of FIG. 3 and a processor.

Referring to FIG. 4, the illustrated monitoring system also includes a memory 140. The memory includes machine readable and machine executable instructions 142 to be followed by a processor described below. The memory may also include data 144 such as lookup tables consulted by the processor during its execution of the instructions. The data in the memory may also include a record of the results of evaluations of the likelihood of patient egress from the bed, for example a record of information just before and just after a change in the evaluation. Communication between the processor and memory is indicated by arrows 146, 148.

The monitoring system also includes processor 160. The processor includes processing circuitry 162 and is adapted to receive data representative of the sensed external parameters. Such data includes presence (or absence) of an object, object attributes as revealed by an RFID tag, and information from the non-RFID components of the sensing system. Certain data received from the non-RFID components may be considered to be attributes of an object. In one example, if the RFID components indicate that a caregiver is nearby but not in the room, and signals from microphone 82 indicate that the caregiver is approaching the room, the system could treat the caregiver's state of motion as an attribute and set its "value" to "approaching". In another example, temperature indicated by temperature sensor 30 may be considered to have not only a magnitude, but also a directional attribute. The system can therefore assign values such as "rising", "stable" or "falling" to the temperature value.

Data flow from the suite of RFID components to the processor is indicated by arrow 164. Data flow from the non-RFID components to the processor is indicated by arrow 166. Data conveyance between components of the monitoring system and data conveyance between the monitoring system and other devices may be carried out over physical pathways or may be carried out without physical pathways.

The processor circuitry 162 is adapted to execute the machine readable instructions 142 thereby causing the monitoring system to evaluate, based on the received data, a likelihood that the occupant of the occupant support will attempt an unauthorized egress from the occupant support. Although the likelihood may be expressed as a numerical probability, it may also be expressed in other ways which are not necessarily as quantitative. For example a likelihood of egress could be a message indicating that the external factors are sufficiently suggestive of an attempted egress to warrant further investigation.

The processor is also adapted to generate a notification signal 170 representing the likelihood that the occupant will attempt an egress and to make the notification available for use by other components of the monitoring system, such as memory 140, or by other devices. Examples of other devices include a video monitor 172 which provides a readout 174 on a display screen 176 informing a viewer of the likelihood of egress. Another example of an other device is a bank of lights 180 (e.g. green, yellow, orange, red) indicating a lesser or greater likelihood of egress depending on the light color. The notification signal 170 is conveyed over an appropriate communication pathway 182, 184 which may be a physical pathway or a nonphysical pathway. Signal 170 will, of course, be a signal compatible with the technical specifications of the destination device 172, 180.

Figure 5:
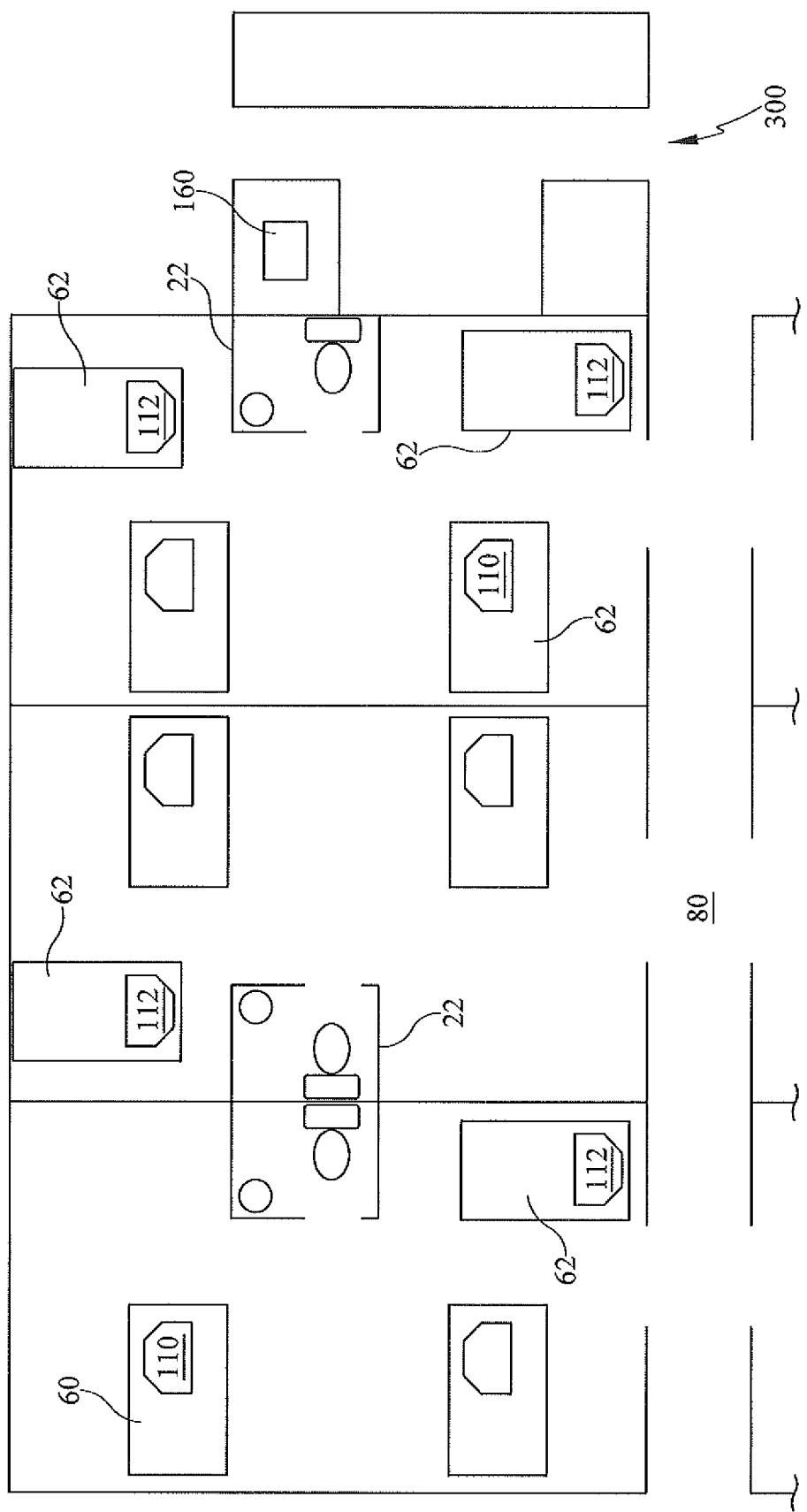
FIG. 5 is a plan view of several hospital rooms and a nearby nurses' station.

Processor 160 may be specific to a given room, bed, or room/bed combination. Alternatively, the processor may be a shared processor located, say, at a nurses' station 300 as seen in FIG. 5.

Figure 6:
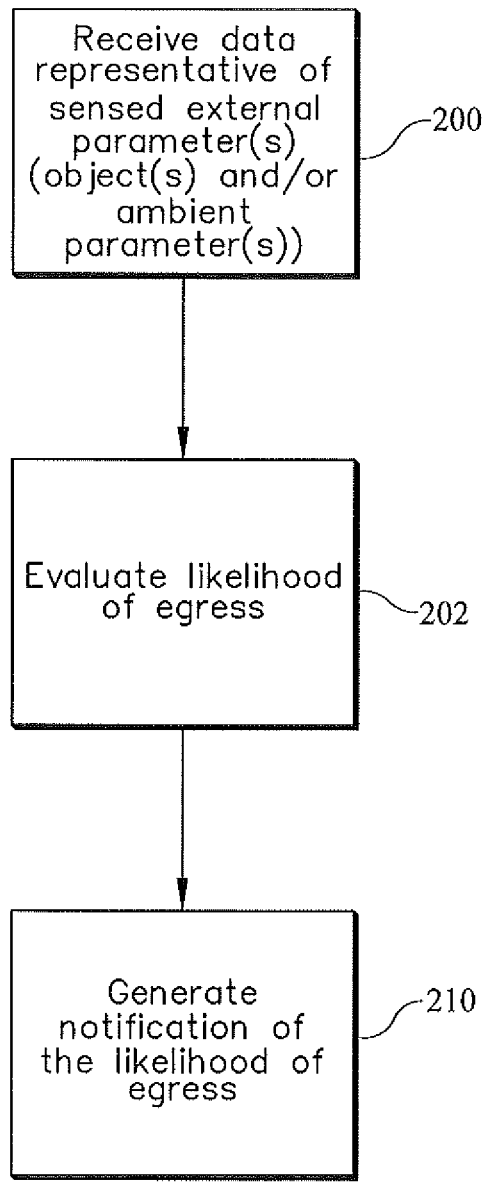
FIG. 6 is a flow chart summmmarizing instructions carried out by the processor of FIG. 4 to predict occupant egress from a hospital bed based on external parameters.

FIG. 6 is a diagram showing the operation of the processor. At block 200 the processor receives the data representative of the external parameters. At block 202 the processor evaluates the likelihood that the occupant will attempt an egress from the occupant support. The evaluated likelihood is based on the received data. At block 210 the processor generates a notification of the likelihood of occupant egress.

Figure 7:
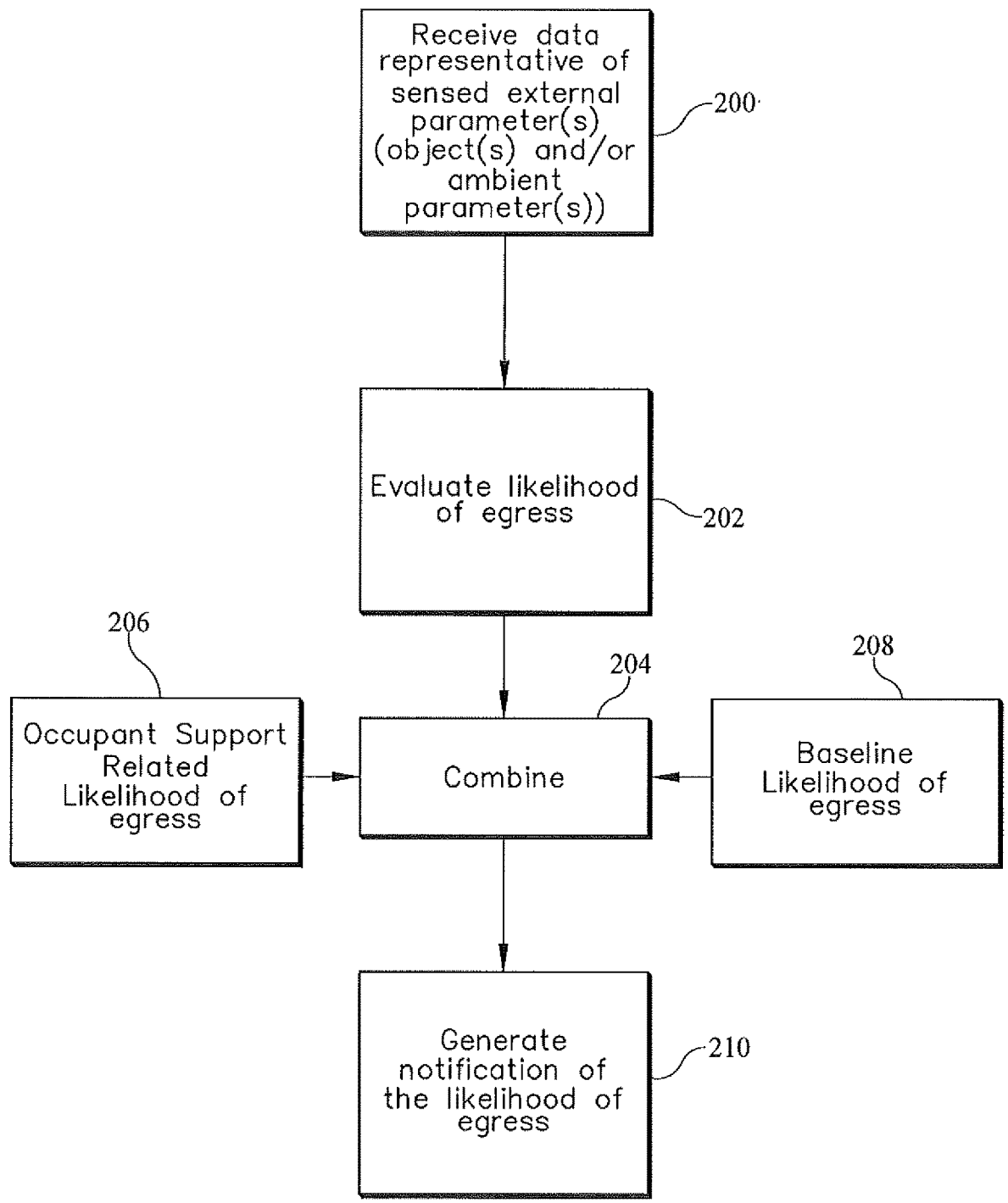
FIG. 7 is a flow chart similar to that of FIG. 6 in which the instructions also account for parameters other than the external parameters.

FIG. 7 is a flow chart similar to that of FIG. 6 illustrating alternative embodiments in which the likelihood of egress based on external parameters from the region of interest is combined with one or more likelihoods of egress based on other sources of information. In comparison to FIG. 6, FIG. 7 includes additional blocks 206 and 208 which account for the likelihood of egress based on factors other than external parameters from the region of interest, and block 204 which aggregates those likelihoods with the evaluated likelihood from block 202. Moreover, the aggregated likelihood of block 204 is considered to be an overall likelihood of egress because it includes the likelihoods of egress based on all the factors considered to be relevant to the prediction, including parameters other than external parameters from the region of interest as described in more detail below. Similarly the notification at block 210 is a notification of the overall likelihood.

Block 206 is a likelihood of unauthorized egress based on factors related to the occupant support itself. One occupant support related factor is the siderail configuration of the bed. Most hospital beds have two or four siderails. In a bed with two siderails, one siderail extends along the left side of the bed and one extends along the right side. A bed with four siderails has a set of two siderails along each side of the bed—one member of each set closer to the head end of the bed and one closer to the foot end. Each of the two or four siderails may be deployed so that its uppermost border is at an elevation higher than the mattress of the bed, or may be stowed so that its uppermost border is below the top of the mattress. The siderail configuration is an accounting of which siderails are deployed and which are stowed. For a bed with four siderails each of the possible sixteen siderail deployed/stowed configurations may be associated with a likelihood of egress.

Another occupant support related factor applies to beds whose mattress support deck can be raised and lowered in elevation relative to the floor. A low elevation of the support deck may be considered to represent a high likelihood of egress; a high elevation of the support deck may be considered to represent a low likelihood of egress; intermediate elevations may represent intermediate likelihoods of egress.

Yet another occupant support related factor is data from a patient position monitoring (PPM) system such as that described in U.S. Pat. No. 6,208,250. The system includes pressure sensors to indicate if the bed occupant has positioned herself on the bed at a location suggestive of impending egress. Such an indication, or the lack thereof, can be used by the monitoring system described herein as a gauge of the likelihood of an unauthorized egress. The data from the PPM system may be used in this way by the system described herein even if the PPM system is disarmed, as long as the PPM sensor data is available.

Block 208 is a "baseline" likelihood of unauthorized egress. The baseline accounts for factors other than the external factors and occupant support related factors. For example a patient may exhibit signs of confusion, recalcitrance, agitation or non-compliance. These signs can be noted, for example in an electronic medical record, and used to establish a baseline likelihood of exit. The baseline likelihood is therefore the likelihood that the occupant will attempt an unauthorized egress even without accounting for the above described external parameters and/or occupant support related factors.

At block 204 the processor combines the external parameter based likelihood from block 202, the occupant support related likelihood from block 206 and the baseline likelihood from block 208 to yield an overall likelihood of occupant egress at block 210. At block 210 the processor generates a notification of the overall likelihood. Alternatively the baseline likelihood 208 need not be used or even determined, in which case the overall likelihood at block 210 reflects only the likelihood based on external factors of block 202 and the occupant support related likelihood of block 206. In another alternative the occupant support related likelihood 206 need not be used or even determined, in which case the overall likelihood at block 210 reflects only the likelihood based on external factors of block 202 and the baseline likelihood of block 208. If neither the baseline nor the occupant support related likelihoods of occupant egress are accounted for the diagram of FIG. 7 reduces to that of FIG. 6. Therefore the likelihood of egress at block 202 of FIG. 6 can be thought of as an overall likelihood of egress because it accounts for all the factors considered to be relevant, namely the external parameters. Likewise the notification at block 210 of FIG. 6 can be thought of as a notification of the overall likelihood of egress.

The evaluated, occupant support related, and baseline likelihoods of blocks 202, 206, 208 may be combined at block 204 in a number of ways. In one example the likelihoods are incremental likelihoods which are added together. In another example the likelihoods are numerical factors which are multiplied together. Either way the factors may be weighted to reflect their relative influences on the likelihood that the occupant will attempt an unauthorized egress. The following table gives a numerical example. Column 3 is a number between zero and one, inclusive, showing the contribution that the indicated factor makes to the possibility that the patient will not exit the bed.

TABLE 1

| Example 1 | | |
|---|---|---|
| 1 Source of Information | 2 Factor | 3 Contribution to Likelihood of not exiting. |
| External (Object(s) and/or Ambient Parameter) | Lavatory within 5 meters | .94 |
| | Walker within 2 meters | .93 |

TABLE 1-continued

| Example 1 | | |
|---|---|---|
| 1 Source of Information | 2 Factor | 3 Contribution to Likelihood of not exiting. |
| Baseline | History of noncompliance | .90 |
| | weak bladder | .89 |
| Occupant Support Related | Deck at lowest elevation | .95 |
| | All siderails Deployed | 1.00 |

Using the values from column 3, three constituents of the overall likelihood of block 210, and the overall likelihood itself can be determined as set forth below:

External Parameter Contribution=0.94×0.93=0.87;

Baseline Contribution=0.90×0.89=0.80;

Occupant Support Contribution=0.95×1.00=0.95;

Overall likelihood of not exiting=0.87×0.80× 0.95=0.66.

In the above example there is a 66% chance that the occupant will not attempt to exit the occupant support, and therefore a 34% likelihood that she will. Notification of the likelihood of egress may be output to a visual display such as video monitor 172, and possibly color coded or otherwise emphasized or de-emphasized consistent with the likelihood of egress. The notification need not take the form of a numerical value. For example the notification could be a simple on/off alarm triggered when the likelihood of egress is higher than a threshold. In another example the notification could be a series of lights 180 as seen in FIG. 4.

The machine readable instructions 142 may be written to carry out a less quantitative, more subjective assessment than the above numerical example. Example 2 below is similar to example 1 but with the following differences: 1) the influences considered in example 1 have been phrased as YES/NO questions, and 2) the numerical contributions of example 1 have been stated as answers to the questions. The questions have been phrased so that a NO answer is "good" in that a NO answer suggests a deterrent to egress and a YES answer is "bad" in that a YES answer suggests an invitation to egress. The overall likelihood of egress at block 210 of the block diagrams may be expressed as a YES or NO depending, for example, on the relative count of YES and NO answers, with the possibility of weighting the answers to reflect their relative importance or value in making the prediction.

TABLE 2

| Example 2 | | | |
|---|---|---|---|
| External Parameter or non-external factor | Question | Answer | Significance (encourages or discourages egress) |
| External (Object(s) | Is a lavatory within 5 meters? | YES | Encourages |

TABLE 2-continued

Example 2

| External Parameter or non-external factor | Question | Answer | Significance (encourages or discourages egress) |
|---|---|---|---|
| and/or Ambient Parameter) | Is a walker within 2 meters? | NO | Discourages |
| | . . . | | |
| Baseline | Does patient have a history of noncompliance? | NO | Discourages |
| | Does patient have a weak bladder? | YES | Encourages |
| | . . . | | |
| Occupant Support Related | Is the deck at its lowest elevation? | NO | Discourages |
| | Are fewer than all siderails deployed? | YES | Encourages |
| | . . . | | |

As an example assume that there are total of 30 questions, equally weighted. The instructions may be set up so that the notification 170 formulated at block 210 is a signal that illuminates a green light if the YES count is no more than 6, a signal that illuminates a yellow light if the YES count is 7 through 9, a signal that illuminates an orange light if the YES count is 10 or 11, and a signal that illuminates a red light if the YES count is 12 or more. This is summarized in table 3 below:

TABLE 3

| YES count | Illumination | Significance (likelihood of unauthorized egress) |
|---|---|---|
| 0-6 | green | Low |
| 7-9 | yellow | Moderate |
| 10-11 | orange | High |
| 12 or more | red | Unacceptable |

Figure 8:
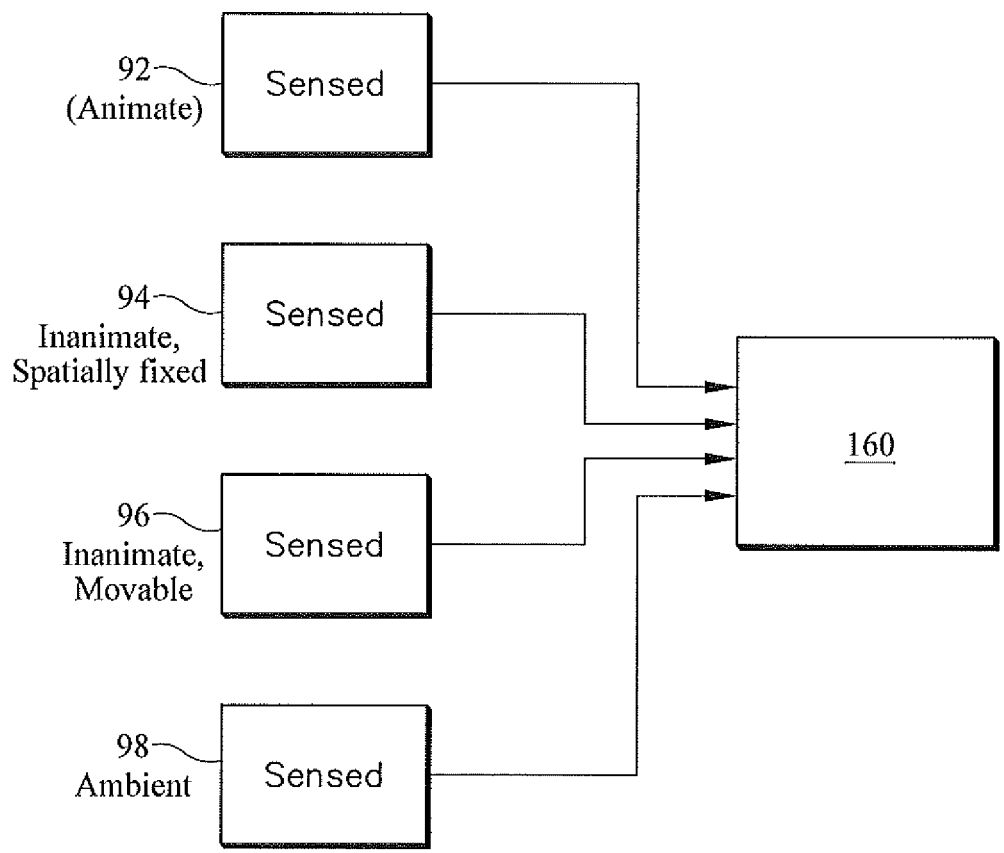
FIG. 8 is a schematic diagram showing a processor receiving inputs from sensors for all four of the classes of external parameters shown in FIG. 2.
Figure 9:
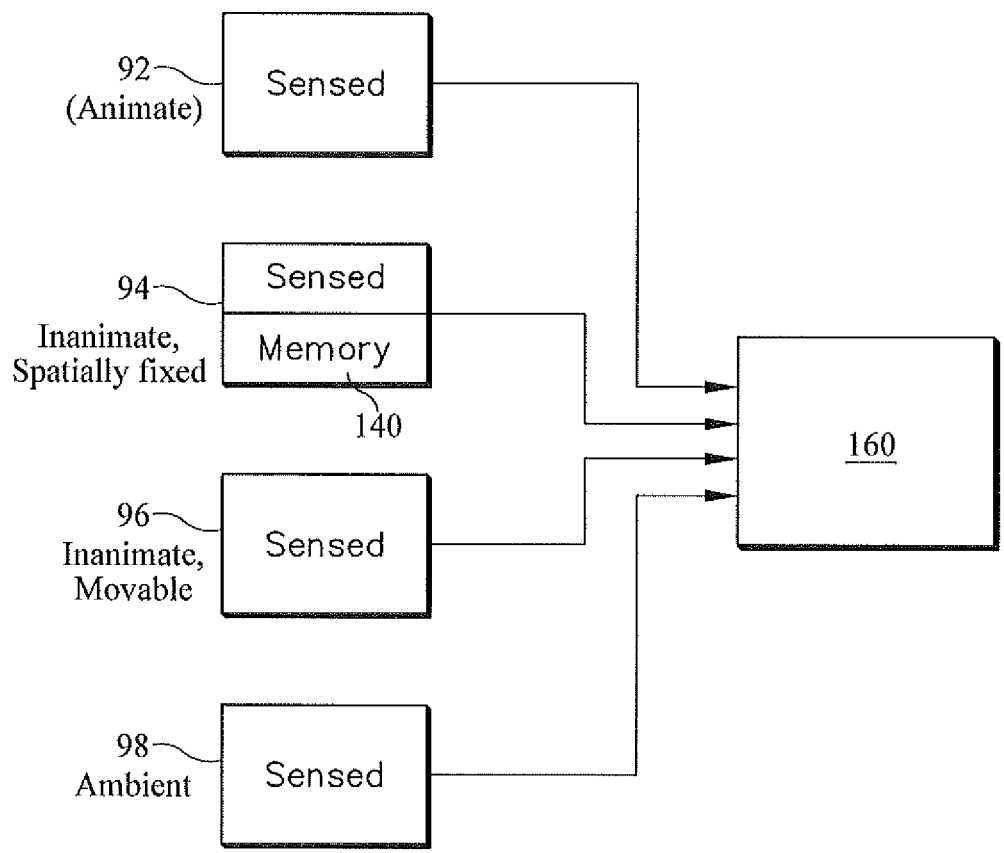
FIG. 9 is a schematic diagram similar to that of FIG. 8 showing the processor receiving inputs from sensors for three of the four classes of external parameters shown in FIG. 2 and receiving inputs for at least some of the parameters of the fourth class from a memory.
Figure 10:
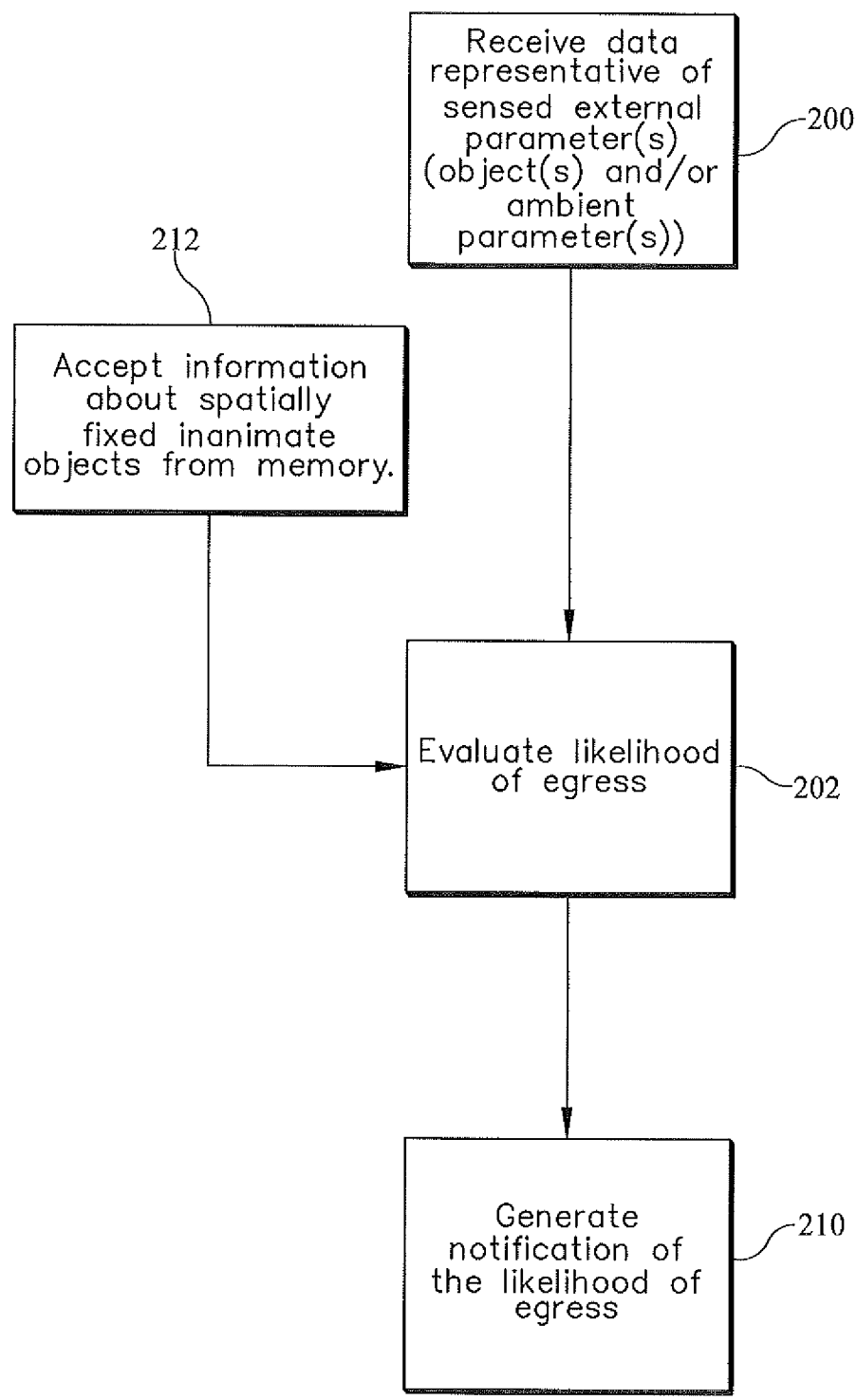
FIG. 10 is a block diagram similar to that of FIG. 6 modified to show the prediction of occupant egress depending on information obtained from a memory as described in connection with FIG. 9.
Figure 11:
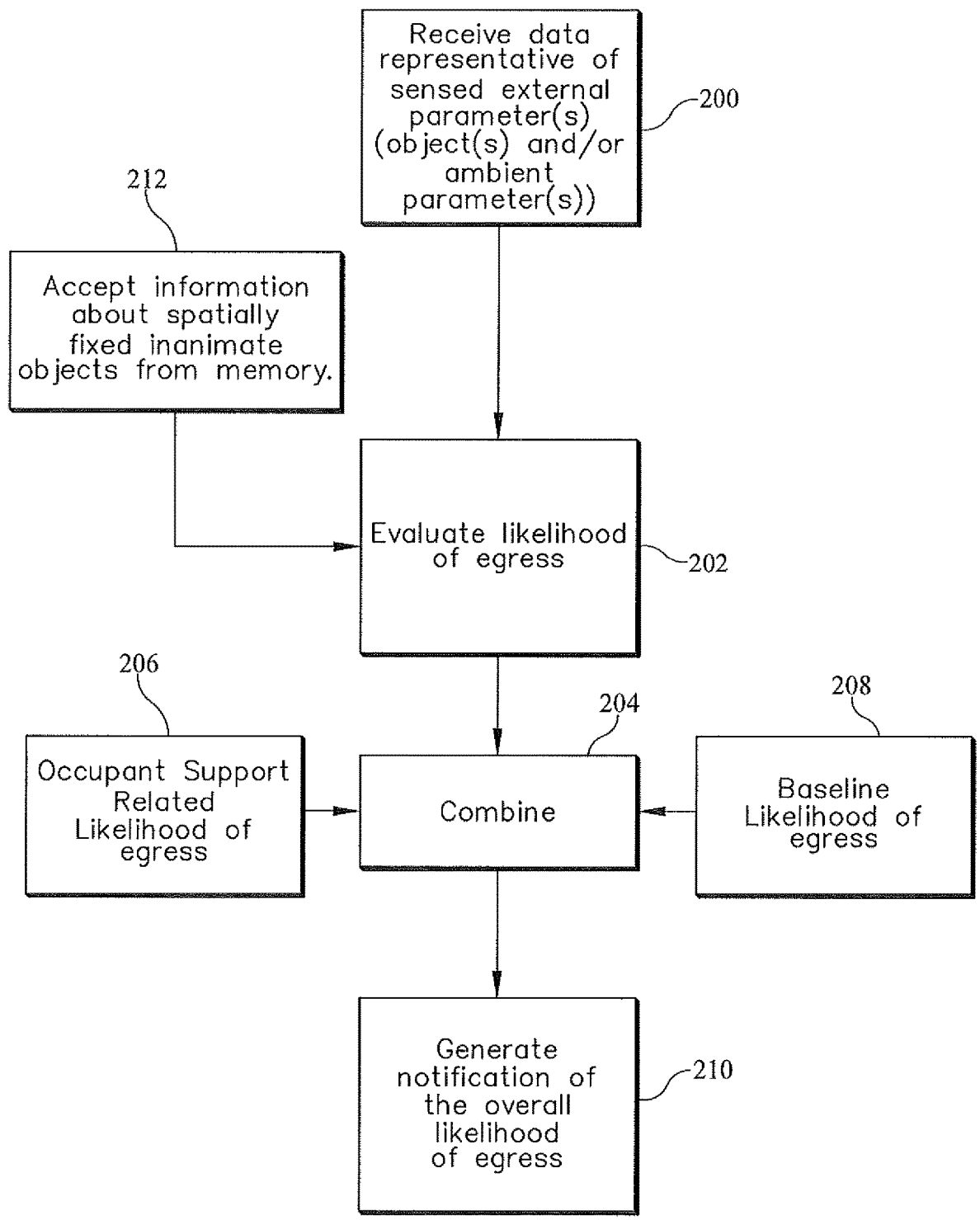
FIG. 11 is a block diagram similar to that of FIG. 7 modified to show the prediction of occupant egress depending on information obtained from a memory as described in connection with FIG. 9.

The system described above uses sensed values of the external parameters. This is illustrated in FIG. 8 which shows processor 160 using sensed values of each of the four classes of parameters 92, 94, 96, 98. As seen in FIG. 9, an alternative approach dispenses with actively sensing at least a subset of the inanimate and spatially fixed parameters even if those objects could influence a patient's decision to attempt an unauthorized egress. In the alternative approach it is unnecessary to attach an RFID tag to the subset of objects to sense their presence or absence. It is also unnecessary to carry out other sensing to ascertain their spatial relationship relative to the occupant support or the occupant. Instead, an indication of their presence and information about their spatial relationship (e.g. location relative to the bed and attributes) can be stored in memory 140 instead of being actively sensed. In this alternative arrangement memory 140 contains certain information about the region of interest, namely information related to the identity, location and attributes of the subset of inanimate, spatially fixed objects. The processor is adapted to accept the information about the subset of objects in the region of interest from memory 140 and, similar to the embodiment previously described, to receive sensed data representative of at least one external parameter not included in the information about the region of interest stored in the memory. The processor is also adapted to execute machine readable instructions thereby causing the monitoring system to evaluate, based on the accepted information and received data, a likelihood that an occupant of the occupant support will engage in unauthorized egress from the occupant support and to generate a notification of the likelihood. Block diagrams summarizing instructions carried out by the processor are shown in FIGS. 10 and 11. FIGS. 10 and 11 are identical to FIGS. 6 and 7 respectively except for the addition of block 212.

The alternative arrangement in which information about at least some of the spatially fixed inanimate objects is stored in memory can work satisfactorily and efficiently in a facility where the layout of all the rooms is substantially identical and the bed is always in a defined position in the room. If the facility includes rooms or other regions of interest which differ substantially from each other, or if the position of the bed within the region of interest is highly variable and not well predictable, the monitoring system can employ a read/write memory. In such a variant, customized information about the layout of a specific room of interest and the spatially fixed inanimate objects in that room can be written to the data region 144 of memory 140. Another variation applies to facilities which contain classes of rooms, for example classes A, B, and C such that the rooms of different classes differ from each other but all the rooms of a given class are substantially the same as each other. In that case the information about the layouts of all the classes of rooms and the inanimate spatially fixed objects in the rooms can be held in memory, and a user need only specify the room class in order for the instructions to use the correct information. In a related variant each class of room will have an RFID tag associated with it. An RFID reader attached to the occupant support or occupant will interrogate the tag to automatically determine the class of the room, and therefore the values of the external parameters stored in memory.

Irrespective of whether the monitoring system relies exclusively on sensing to acquire the values of all the external parameters as in FIGS. 6-8, or accepts information related to at least some inanimate spatially fixed parameters from memory as in FIGS. 9-11, the system may be configured to assess the effects of the object related parameters, but not the effects of the ambient parameters. Similar to the monitoring system already described, such a system includes a sensing subsystem adapted to sense an external object within the region of interest and a memory containing instructions which are machine readable and machine executable. The system also includes a processor adapted to receive data or accept information from memory representative of the sensed external object. The processor is also adapted to execute machine readable instructions thereby causing the monitoring system to evaluate, based on the received data and accepted information, a likelihood that the occupant will attempt an unauthorized egress from the occupant support. The processor is also adapted to generate a notification of the likelihood of occupant egress.

In another embodiment the monitoring system may be configured to assess the effects of the ambient parameters, but not the effects of the object related parameters. Similar to the monitoring systems already described, such a system includes a sensing subsystem adapted to sense an ambient parameter within the region of interest relative to the occupant support. The system also includes a processor adapted to receive data representative of the sensed ambient parameter and to execute the machine readable instructions thereby causing the monitoring system to evaluate, based on the received data, a likelihood that an occupant of the occupant support will engage in unauthorized egress from the occupant support. The processor is also adapted to generate a notification of the likelihood of unauthorized egress.

In much of the foregoing description the region of interest is equated to a hospital room. However as explained in connection with assessing whether a caregiver is approaching or moving away, the region of interest may differ from a hospital room. By way of example the region of interest may encompass less than an entire room, may include an entire room and its environs (e.g. at least part of an adjoining corridor) or may include part of a room and its environs outside the room. The region of interest my be bounded by the range of the various sensors or may be bounded by machine readable instructions which disregard data originating beyond a certain range.

The foregoing description concerns itself predominantly with predicting an unauthorized egress. However the system can also be used, if desired, to predict authorized egress.

The terms "substantially" and "about" may be used herein to represent the inherent degree of uncertainty that may be attributed to any quantitative comparison, value, measurement or other representation. These terms are also used herein to represent the degree by which a quantitative representation may vary from a stated reference without resulting in a change in the basic function of the subject matter at issue.

Although this disclosure refers to specific embodiments, it will be understood by those skilled in the art that various changes in form and detail may be made without departing from the subject matter set forth in the accompanying claims.

We claim:

1. A monitoring system comprising:
   a sensing subsystem adapted to sense an external parameter within a region of interest relative to an occupant support or an occupant of the occupant support; and
   a processor adapted to:
   1) receive data representing the sensed external parameter;
   2) execute machine readable instructions thereby causing the monitoring system to evaluate, based on the received data, a likelihood that the occupant will attempt an egress from the occupant support; and
   3) generate a notification of the likelihood.

2. The system of claim 1 wherein the likelihood generated by the processor by executing the machine readable instructions is an overall likelihood which accounts for the sensed external parameter and also accounts for at least one of
   1) a baseline likelihood that the occupant will attempt egress, and
   2) an occupant support related likelihood that the occupant will attempt egress, and
   wherein neither the baseline likelihood nor the occupant support related likelihood is based on the data representing the sensed external parameter.

3. The system of claim 2 wherein the occupant support related likelihood depends on at least one of a siderail configuration, a support deck elevation, and a reading from a patient position monitoring system.

4. The system of claim 1 wherein the sensed external parameter is related to one or more of 1) an animate object, 2) an inanimate, spatially fixed object, 3) an inanimate, movable object and 4) an ambient condition.

5. The system of claim 1 wherein the sensing subsystem includes a suite of RFID components.

6. The system of claim 5 wherein the sensed external parameter is related to an object and the suite of RFID components includes an RFID reader associated with the occupant support or occupant and an RFID tag associated with the object.

7. The system of claim 6 wherein the object is a person.

8. The system of claim 6 wherein the object is a person, the tag reveals at least one attribute of the person and the received data includes the attribute.

9. The system of claim 8 wherein the attribute is one or more of:
   a) a distinction between an authority figure and a non-authority figure;
   b) an authoritativeness status of a person.

10. The system of claim 1 wherein the received data includes an attribute of the sensed external parameter.

11. The system of claim 1 wherein the external parameter is a parameter representing an object or a condition in the region of interest and wherein the region of interest does not include either the occupant support or the occupant.

12. The system of claim 11 wherein the object in the region of interest does not include objects which are inherent or commonplace components of a hospital bed.

13. The system of claim 11 wherein the object in the region of interest does not include objects supported on the bed and provided on an as-needed basis to serve the needs of selected occupants.

14. A monitoring system comprising:
   a memory containing information about a region of interest relative to an occupant support; and
   a processor adapted to
   1) accept the information about the region of interest from the memory;
   2) receive data representative of at least one external parameter not included in the information about the region of interest stored in the memory;
   3) execute machine readable instructions thereby causing the monitoring system to evaluate, based on the accepted and received information, a likelihood that an occupant of the occupant support will attempt egress from the occupant support; and
   4) generate a notification of the likelihood.

15. The monitoring system of claim 14 wherein the information in the memory about the region of interest is information about an inanimate and spatially fixed object in the region of interest.

16. The monitoring system of claim 15 wherein the information in the memory about the region of interest is information about at least one of the identity of the object and the spatial relationship between the object and the occupant support or the occupant.

17. The system of claim 14 wherein the memory is a read/write memory.

18. The system of claim 14 wherein the external parameter is related to one or more of 1) an animate object, 2) an inanimate, spatially fixed object, 3) an inanimate, movable object and 4) an ambient condition.

19. The system of claim 14 wherein the likelihood generated by the processor by executing the machine readable instructions is an overall likelihood which accounts for the accepted information about the region of interest from the memory and the received data representative of at least one external parameter, and also accounts for at least one of
   1) a baseline likelihood that the occupant will attempt egress, and
   2) an occupant support related likelihood that the occupant will attempt egress, and wherein neither the baseline likelihood nor the occupant support related likelihood is based on either or both of the accepted information about the region of interest from the memory and the received data representative of at least one external parameter.

* * * * *